US00PP36443P3

(12) United States Plant Patent
Schoone

(10) Patent No.: US PP36,443 P3
(45) Date of Patent: Feb. 11, 2025

(54) ***PHALAENOPSIS* PLANT NAMED 'Tambourine Girl'**

(50) Latin Name: *Phalaenopsis hybrida*
Varietal Denomination: Tambourine Girl

(71) Applicant: FLORICULTURA B.V., Heemskerk (NL)

(72) Inventor: Rene Schoone, Assendelft (NL)

(73) Assignee: FLORICULTURA B.V., Heemskerk (NL)

( * ) Notice: Subject to any disclaimer, the term of this patent is extended or adjusted under 35 U.S.C. 154(b) by 0 days.

(21) Appl. No.: 18/625,193

(22) Filed: Apr. 2, 2024

(65) Prior Publication Data

US 2024/0334858 P1 Oct. 3, 2024

Related U.S. Application Data

(60) Provisional application No. 63/456,505, filed on Apr. 2, 2023.

(51) Int. Cl.
*A01H 5/02* (2018.01)
*A01H 6/62* (2018.01)

(52) U.S. Cl.
USPC ..... Plt./311
CPC ..... *A01H 6/62* (2018.05)

(58) Field of Classification Search
USPC ..... Plt./311
CPC ..... A01H 5/02
See application file for complete search history.

*Primary Examiner* — Kent L Bell
(74) *Attorney, Agent, or Firm* — C. Anne Whealy

(57) ABSTRACT

A new and distinct cultivar of *Phalaenopsis* plant named 'Tambourine Girl', characterized by its upright plant habit; moderately vigorous growth habit; strong flowering stems; strong leaves; freely flowering habit with typically two inflorescences developing per plant, each inflorescence with numerous flowers; flowers with purplish pink-colored petals; and good postproduction longevity.

2 Drawing Sheets

Figure 1:
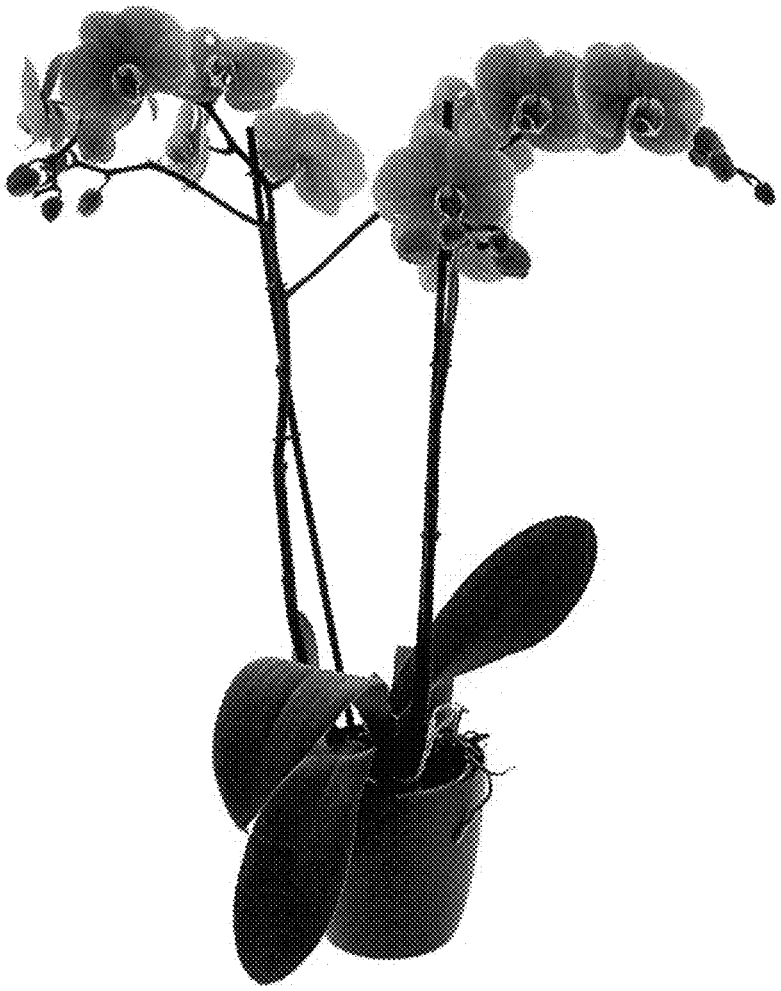

Botanical designation: *Phalaenopsis hybrida.*
Cultivar denomination: 'TAMBOURINE GIRL'.

STATEMENT REGARDING PRIOR DISCLOSURES BY INVENTOR AND APPLICANT/ASSIGNEE

An European Community Plant Breeder's Rights application for the instant plant was filed by the Applicant/Assignee of the instant application, Floricultura B. V. of Heemskerk, The Netherlands on Feb. 27, 2023, application number 2023/0530. Foreign priority is not claimed to this application.

The Inventor and Applicant/Assignee assert that no sales, offers for sale or public distribution of the instant plant occurred more than one year prior to the effective filing date of this application.

Any information about the claimed plant would have been obtained from a direct or indirect disclosure from the Inventor and/or Applicant/Assignee. Inventor and Applicant/Assignee claim a prior art exception under 35 U.S.C. 102(b)(1) for disclosures and/or sales prior to the filing date but less than one year prior to the effective filing date.

BACKGROUND OF THE INVENTION

The present invention relates to a new and distinct cultivar of *Phalaenopsis* plant, botanically known as *Phalaenopsis hybrida*, and hereinafter referred to by the name 'Tambourine Girl'.

The new *Phalaenopsis* plant is a product of a planned breeding program conducted by the Inventor in Nantou, Taiwan and Heemskerk, The Netherlands. The objective of the breeding program is to develop new fast-growing and freely flowering *Phalaenopsis* plants with good leaf shape and flowers with unique and attractive patterns and coloration.

The new *Phalaenopsis* plant originated from a cross-pollination in March 2013 in Nantou, Taiwan of *Phalaenopsis hybrida* 'Happy Helo', not patented, as the female, or seed, parent with *Phalaenopsis hybrida* 'Hilo Lip' X 'Maki Watanabe', not patented, as the male, or pollen, parent. The new *Phalaenopsis* plant was discovered and selected by the Inventor as a single flowering plant from within the progeny of the stated cross-pollination grown in a controlled greenhouse environment in Heemskerk, The Netherlands in October 2019.

Asexual reproduction of the new *Phalaenopsis* plant by in vitro meristem propagation in a controlled environment in Assendelft, The Netherlands since October 2020 has shown that the unique features of this new *Phalaenopsis* plant are stable and reproduced true to type in successive generations.

SUMMARY OF THE INVENTION

Plants of the new *Phalaenopsis* have been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Tambourine Girl'. These characteristics in combination distinguish 'Tambourine Girl' as a new and distinct *Phalaenopsis* plant:

1. Upright plant habit.
2. Moderately vigorous growth habit.
3. Strong flowering stems.

4. Strong leaves.
5. Freely flowering habit with typically two inflorescences developing per plant, each inflorescence with numerous flowers.
6. Flowers with purplish pink-colored petals.
7. Good postproduction longevity.

Plants of the new *Phalaenopsis* can be compared to plants of the female parent, 'Happy Helo'. Plants of the new *Phalaenopsis* differ primarily from plants of 'Happy Helo' in petal color as petals of plants of the new *Phalaenopsis* are not striped or netted whereas petals of plants of 'Happy Helo' are striped and netted. In addition, the cirrhose tips of plants of the new *Phalaenopsis* are white in color whereas the cirrhose tips of plants of 'Happy Helo' are purple in color.

Plants of the new *Phalaenopsis* can be compared to plants of the male parent, 'Hilo Lip' X 'Maki Watanabe'. Plants of the new *Phalaenopsis* differ primarily from plants of 'Hilo Lip' X 'Maki Watanabe' in flower color as flowers of plants of the new *Phalaenopsis* are purplish pink in color whereas flowers of plants of 'Hilo Lip' X 'Maki Watanabe' are purplish pink in color with white-colored centers.

Plants of the new *Phalaenopsis* can be compared to plants of *Phalaenopsis hybrida* 'Tigris', disclosed in U.S. Plant Pat. No. 30,688. In side-by-side comparisons, plants of the new *Phalaenopsis* differ primarily from plants of 'Tigris' in the following characteristics:

1. Flowers of plants of the new *Phalaenopsis* are purplish pink in color whereas flowers of plants of 'Tigris' are purple violet in color with white-colored centers.
2. Labellum of plants of the new *Phalaenopsis* are white, reddish purple and yellow in color whereas the labellum of plants of 'Tigris' is violet and purplish red in color.
3. Cirrhose tips of the labellum of plants of the new *Phalaenopsis* are white in color whereas cirrhose tips of the labellum of plants of 'Tigris' are violet in color.

BRIEF DESCRIPTION OF THE PHOTOGRAPHS

The accompanying photographs illustrate the overall appearance of the new *Phalaenopsis* plant showing the colors as true as it is reasonably possible to obtain in colored reproductions of this type. Colors in the photographs may differ slightly from the color values cited in the detailed botanical description which accurately describe the colors of the new *Phalaenopsis* plant.

The photograph on the first sheet (FIG. 1) is a side perspective view of a typical flowering plant of 'Tambourine Girl' grown in a container.

Figure 2:
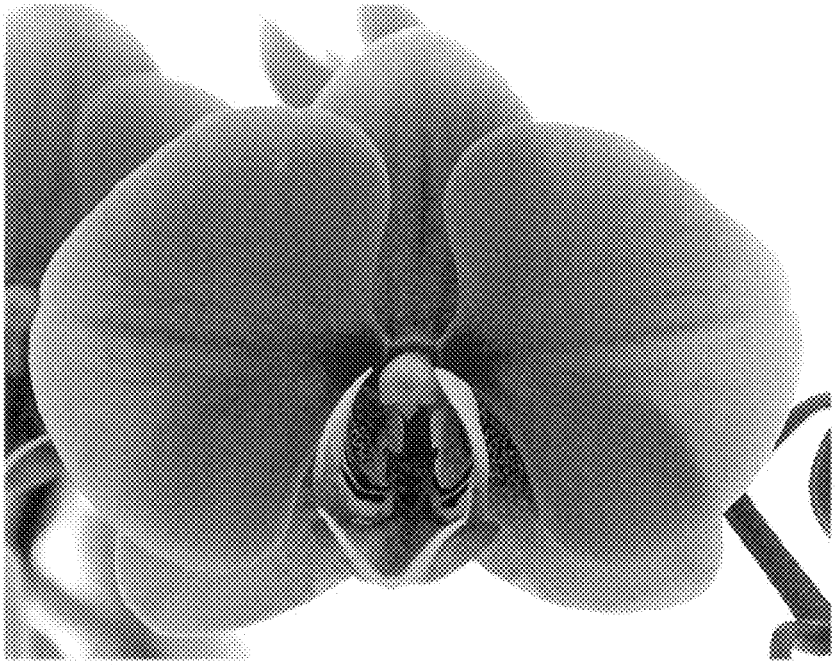

The photograph on the second sheet (FIG. 2) is a close-up view of a typical flower of 'Tambourine Girl'.

DETAILED BOTANICAL DESCRIPTION

The aforementioned photographs and following observations and measurements describe plants grown during the autumn in 10.5-cm containers in a glass-covered greenhouse in Heemskerk, The Netherlands and under cultural practices typically used in commercial *Phalaenopsis* production. Plants were 18 months old when the photographs and description were taken. During the first twelve months of production of the plants, day and night temperatures averaged 27° C. During the final six months of production of the plants, day temperatures ranged from 20° C. to 22° C. and night temperatures ranged from 18° C. to 20° C. During the production of the plants, light levels ranged from a minimum of 5,000 lux to a maximum of 10,000 lux. In the following description, color references are made to The Royal Horticultural Society Colour Chart, 2015 Edition, except where general terms of ordinary dictionary significance are used.

Botanical classification: *Phalaenopsis hybrida* 'Tambourine Girl'.

Parentage:

*Female, or seed, parent.*—*Phalaenopsis hybrida* 'Happy Helo', not patented.

*Male, or pollen, parent.*—*Phalaenopsis hybrida* 'Hilo Lip' X 'Maki Watanabe', not patented.

Propagation:

*Type.*—By in vitro meristem propagation.

*Time to initiate roots, summer and winter.*—About two weeks at temperatures about 28° C. to 30° C.

*Time to produce a rooted young plant, summer and winter.*—About 20 to 25 weeks at temperatures about 28° C. to 30° C.

*Root description.*—Thin, fibrous; typically light yellowish white in color; actual color of the roots is dependent on substrate composition, water quality, fertilizer, substrate temperature and age of roots.

*Rooting habit.*—Freely branching; medium density.

Plant description:

*Plant form and growth habit.*—Herbaceous epiphyte; upright plant habit with typically two inflorescences developing per plant, each inflorescence with numerous flowers; monopodial; moderately vigorous growth habit and moderate growth rate.

*Plant height, substrate level to top of foliar plane.*—About 13.4 cm.

*Plant height, substrate level to top of floral plane.*—About 47.8 cm.

*Plant diameter or spread.*—About 37.5 cm.

Leaf description:

*Arrangement and quantity.*—Distichous, simple; sessile; about five fully-developed leaves per plant.

*Length.*—About 20.5 cm.

*Width.*—About 6.2 cm.

*Aspect.*—Semi-erect to outwardly arching.

*Shape.*—Oblanceolate to obovate; slightly carinate.

*Apex.*—Unequal and broadly acute.

*Base.*—Sheathing. Sheath length: About 1.8 cm. Sheath width: About 1 cm. Sheath color: Upper surface, close to between N186C and 200B; lower surface, close to 144B.

*Margin.*—Entire; slightly revolute.

*Texture and luster, upper and lower surfaces.*—Smooth, glabrous; slightly glossy.

*Venation pattern.*—Camptodromous.

*Color.*—Developing leaves, upper surface: Close to 143B. Developing leaves, lower surface: Close to 146B; margins, strongly tinged with close to N186C. Fully expanded leaves, upper surface: Close to between 137A and 146A; venation, close to NN137A. Fully expanded leaves, lower surface: Close to 146B; towards the margins, strongly tinged with close to N186C; venation, close to 148B moderately tinged with close to N186C.

Inflorescence description:

*Appearance and flowering habit.*—Showy zygomorphic flowers arranged on axillary simple or branched racemes; typically two inflorescences develop per plant; each inflorescence with about 16 flowers;

flowers face outwardly on outwardly arching inflorescences supported by upright peduncles; flowers with three petals, two lateral petals and one center petal transformed into a labellum and three sepals.

*Fragrance*.—None detected.

*Time to flower*.—Plants begin flowering about six months after planting; plants flower naturally during the winter into the spring.

*Flower longevity*.—Long flowering period, individual flowers maintain good substance for about eight weeks on the plant; flowers not persistent.

*Inflorescence length* (*lowermost flower to inflorescence apex*).—About 28.4 cm.

*Inflorescence width*.—About 22.4 cm.

*Flower buds*.—Height: About 2.2 cm. Diameter: About 1.7 cm by 2.2 cm. Shape: Broadly ovate. Color: Close to N77B and tinged with close to 148A to 148C.

*Flower size*.—About 7.3 cm (vertical) by 8.5 cm (horizontal).

*Flower depth*.—About 3.8 cm.

*Petals, quantity and arrangement*.—Three, two lateral petals and one center petal transformed into a labellum.

*Lateral petals*.—Length: About 4.1 cm. Width: About 5.6 cm. Shape: Roughly reniform. Apex: Rounded. Margin: Entire; not undulate. Texture and luster, upper and lower surfaces: Smooth, glabrous; moderately velvety; matte. Color: When opening, upper surface: Close to between NN78C and N80B; towards the apex and margins, close to N80B to N80D; at the base, close to N78A. When opening, lower surface: Close to 76B; towards the margins and apex, close to N78D. Fully opened, upper surface: Close to N78C; towards the apex and margins, close to N78D; outer margins, close to 76C; at the base, close to N78A. Fully opened, lower surface: Close to 84C; towards the margins, tinged with close to N80D.

*Labella*.—Appearance: Three-parted with two lateral lobes and a central lobe. Length, lateral lobes: About 2.1 cm. Width, lateral lobes: About 1.4 cm. Length, central lobe: About 3.2 cm. Width, central lobe: About 0.7 cm to 2 cm. Length, cirrhose tips: About 1.7 cm. Shape, lateral lobes: Obovate. Shape, central lobe: Deltoid. Apex, lateral lobes: Obtuse. Apex, central lobe: Cleft with two backwardly curled cirrhose tips. Margins, lateral and central lobes: Entire. Texture and luster, lateral and central lobes, upper and lower surfaces: Smooth, glabrous, moderately velvety; matte. Callosities: Located at the base of the labellum and attachment point of the lateral petals; about 4.5 mm in length, about 5 mm in width and about 5 mm in height. Color: When opening, upper surface: Lateral lobes: Close to NN155D; central blotch, close to NN78C to NN78D; at the base, slightly blotched with close to 22B and stripes, close to 59A. Central lobe: Close to 77C; central blotch, close to N78C to N78D; at the margins, tinged with close to 165C to 165D; at the base, close to 59A and N81B with stripes, close to 11D; cirrhose tips, close to NN155D. When opening, lower surface: Lateral lobes: Close to N155A; upper margins, close to N74C; lower margins, close to 22B. Central lobe: Close to 76C; towards the base, close to 163A to 163B and at the base, close to N78A to N78B; cirrhose tips, close to NN155D. Fully opened, upper surface: Lateral lobes: Close to NN155D; central blotch, close to NN78C; at the base, slightly blotched with close to 22A to 22B and stripes, close to 59A. Central lobe: Close to 77D; central blotch, close to N78C to N78D; at the margins, tinged with close to 165C to 165D; at the base, close to 59A and N81B with stripes, close to 11D; cirrhose tips, close to NN155D. Fully opened, lower surface: Lateral lobes: Close to N155A; upper margins, close to N74C; lower margins, close to 22B. Central lobe: Close to 76C; towards the base, close to 163A to 163B and at the base, close to N78A to N78B; cirrhose tips, close to NN155D. Callosities: When developing: Close to 11A with fine dots, close to 59A. Fully developed: Close to 13B with fine dots, close to 59A.

*Sepals*.—Quantity and arrangement: Three, one upper dorsal sepal and two lower lateral sepals. Length, dorsal sepal: About 4.2 cm. Width, dorsal sepal: About 3.5 cm. Length, lateral sepals: About 4.2 cm. Width, lateral sepals: About 2.7 cm. Shape, dorsal sepal: Broadly elliptic. Shape, lateral sepals: Ovate. Apex, dorsal sepal: Obtuse. Apex, lateral sepals: Bluntly and broadly acute. Base, dorsal and lateral sepals: Cuneate. Margins, dorsal and lateral sepals: Entire; not undulate. Texture and luster, dorsal and lateral sepals, upper surface: Smooth, glabrous; velvety; matte. Texture and luster, dorsal and lateral sepals, lower surface: Smooth, glabrous; slightly velvety; slightly glossy. Color, dorsal sepal: When opening, upper surface: Close to NN78C; towards the apex and margins, close to N80D; at the base, close to N78A; venation, close to N78A. When opening, lower surface: Close to 77C; towards the base, slightly tinged with close to 148C. Fully opened, upper surface: Close to N78C; towards the apex and margins, close to N78D; outer margins, close to 76C; at the base, close to N78A. Fully opened, lower surface: Close to 84C; towards the margins, slightly tinged with close to N80D. Color, lateral sepals: When opening, upper surface: Close to N78B; towards the apex, close to 75D; centers, close to N79C with fine dots, close to N79B. When opening, lower surface: Close to N77B; towards the base, tinged with close to 148B. Fully opened, upper surface: Close to N78D; towards the apex, close to between 84C and 84D; centers with fine dots, close to N79C; at the base, close to N78A to N78B; venation, close to N78A to N78B. Fully opened, lower surface: Close to 77D; towards the base, tinged with close to 148C; main vein, close to 77C.

*Peduncles*.—Length: About 57.6 cm. Diameter: About 7 mm. Strength: Strong. Aspect: Upright to outwardly arching. Texture and luster: Smooth, glabrous; matte. Color: Darker than between 147A and N189A covered with fine dots, close to 146D.

*Pedicels*.—Length: About 2.7 cm. Diameter: About 3 mm. Strength: Moderately strong. Aspect: About 65° from peduncle axis. Texture and luster: Smooth, glabrous; matte. Color: Close to 147C; proximally, close to 148A.

*Reproductive organs*.—Androecium: Column length: About 9 mm. Column width: About 6 mm. Column color: Close to N75A; distally, close to N76C. Pollinia quantity: Two. Pollinia diameter (per two pollinia): About 3 mm. Pollinia color: Close to 25A. Gynoecium: Stigma length: About 3 mm. Stigma width: About 5 mm. Stigma shape: Reniform. Stigma color: Close to NN155D. Ovary length: About 9 mm. Ovary diameter: About 2 mm. Ovary color: Close to 148D strongly tinged with close to 75B. Seeds and fruits: To date, seed and fruit development have not been observed on plants of the new *Phalaenopsis*.

Pathogen & pest resistance: To date, plants of the new *Phalaenopsis* have not been shown to be resistant to pathogens and pests common to *Phalaenopsis* plants.

Temperature tolerance: Plants of the new *Phalaenopsis* have been observed to tolerate high temperatures about 40° C. and are suitable for USDA Hardiness Zones 10 to 12.

It is claimed:

1. A new and distinct *Phalaenopsis* plant named 'Tambourine Girl' as illustrated and described.

* * * * *